(12) United States Patent
Patzer

(10) Patent No.: US 7,302,960 B2
(45) Date of Patent: Dec. 4, 2007

(54) MOMENTARY HIGH PRESSURE VALVE

(75) Inventor: Charles R. Patzer, Columbus, OH (US)

(73) Assignee: Smiths Medical ASD, Inc., Rockland, MA (US)

( * ) Notice: Subject to any disclaimer, the term of this patent is extended or adjusted under 35 U.S.C. 154(b) by 211 days.

(21) Appl. No.: 11/163,660

(22) Filed: Oct. 26, 2005

(65) Prior Publication Data

US 2007/0089787 A1   Apr. 26, 2007

(51) Int. Cl.
*F16K 11/02*   (2006.01)
(52) U.S. Cl. .................... 137/12; 137/112; 604/83
(58) Field of Classification Search ........... 137/111, 137/112 I, 114, 517, 12; 251/5; 604/34, 604/83 X
See application file for complete search history.

(56) References Cited

U.S. PATENT DOCUMENTS

| | | | | |
|---|---|---|---|---|
| 2,829,674 A * | 4/1958 | Segelhorst et al. | ......... | 137/504 |
| 3,066,767 A | 12/1962 | Djordjevitch | ................ | 188/88 |
| 3,967,645 A | 7/1976 | Gregory | ................ | 137/525.1 |
| 4,106,491 A | 8/1978 | Guerra | ........................ | 128/2 F |
| 4,341,239 A | 7/1982 | Atkinson | ..................... | 137/493 |
| 4,434,810 A | 3/1984 | Atkinson | ..................... | 137/493 |
| 4,436,519 A | 3/1984 | O'Neill | ...................... | 604/175 |
| 4,524,805 A | 6/1985 | Hoffman | ..................... | 137/846 |
| 4,535,818 A | 8/1985 | Duncan et al. | ............. | 137/846 |
| 4,535,819 A | 8/1985 | Atkinson et al. | ........... | 137/846 |
| 4,535,820 A | 8/1985 | Raines | ........................ | 137/854 |
| 4,556,086 A | 12/1985 | Raines | ........................ | 137/852 |
| 4,566,493 A | 1/1986 | Edwards et al. | ............ | 137/846 |
| 4,612,960 A | 9/1986 | Edwards et al. | ............ | 137/846 |
| 4,666,429 A | 5/1987 | Stone | | |
| 4,683,916 A | 8/1987 | Raines | ....................... | 137/854 |
| 4,729,401 A | 3/1988 | Raines | ....................... | 137/512 |
| 4,758,224 A | 7/1988 | Siposs | ........................ | 604/119 |
| 4,819,684 A | 4/1989 | Zaugg et al. | ............... | 137/112 |

(Continued)

FOREIGN PATENT DOCUMENTS

EP   0630661 A1   12/1994

(Continued)

OTHER PUBLICATIONS

International Search Report for PCT/US2006/041378, mailed Mar. 1, 2007 (3 pages).

(Continued)

*Primary Examiner*—Stephen M. Hepperle
(74) *Attorney, Agent, or Firm*—Wood, Herron & Evans, LLP

(57) ABSTRACT

A valve (10) comprises a housing (12) with a valve element (14) which normally fluidicly couples a low pressure operating device, such as a transducer (30) and tubing (34) to be coupled to a patient (36) along a first flow path (42) including a flexible control wall (58) which normally interrupts a second flow path (72) between a high pressure generating source such as an injector syringe (32) and the tubing (34), but which flexes, in response to high pressure excursions from the syringe (32) to allow the second flow path (72) to open as it flexes into the first flow path (42) to thereby restrict same thus providing protection to the transducer (30) during the high pressure excursion from the syringe (32).

39 Claims, 5 Drawing Sheets

U.S. PATENT DOCUMENTS

| | | | | |
|---|---|---|---|---|
| 4,960,412 A | 10/1990 | Fink | ............................ | 604/167 |
| 5,010,925 A | 4/1991 | Atkinson et al. | ............ | 137/847 |
| 5,070,905 A | 12/1991 | Paradis | ........................ | 137/606 |
| 5,098,405 A | 3/1992 | Peterson et al. | ............ | 604/247 |
| 5,176,658 A | 1/1993 | Ranford | ........................ | 604/247 |
| 5,190,067 A | 3/1993 | Paradis et al. | .................. | 137/1 |
| 5,261,459 A | 11/1993 | Atkinson et al. | ............ | 137/846 |
| 5,269,771 A | 12/1993 | Thomas et al. | .............. | 604/213 |
| 5,301,707 A | 4/1994 | Hofsteenge | ................... | 137/12 |
| 5,474,099 A | 12/1995 | Boehmer et al. | .............. | 137/15 |
| 5,520,661 A | 5/1996 | Lal et al. | ..................... | 604/246 |
| 5,578,059 A | 11/1996 | Patzer | ......................... | 604/249 |
| 5,685,866 A * | 11/1997 | Lopez | ......................... | 604/256 |
| 5,775,671 A | 7/1998 | Cote, Sr. | .................. | 251/149.8 |
| 5,810,768 A | 9/1998 | Lopez | ........................... | 604/56 |
| 6,044,859 A | 4/2000 | Davis | ........................... | 137/15 |
| 6,059,747 A | 5/2000 | Bruggeman et al. | ........... | 604/49 |
| 6,083,194 A | 7/2000 | Lopez | ......................... | 604/28 |
| 6,245,048 B1 | 6/2001 | Fangrow, Jr. et al. | ........ | 604/249 |
| 6,428,520 B1 | 8/2002 | Lopez et al. | ................. | 604/249 |
| 6,569,117 B1 | 5/2003 | Ziv et al. | ................ | 604/164.01 |
| 6,767,340 B2 | 7/2004 | Willis et al. | ................. | 604/256 |
| 6,866,654 B2 | 3/2005 | Callan et al. | ................ | 604/247 |

FOREIGN PATENT DOCUMENTS

| | | |
|---|---|---|
| WO | 9640359 A1 | 12/1996 |
| WO | 03015851 A1 | 2/2003 |

OTHER PUBLICATIONS

Written Opinion for PCT/US2006/041378, mailed Mar. 1, 2007 (5 pages).

* cited by examiner

MOMENTARY HIGH PRESSURE VALVE

FIELD OF THE INVENTION

The present invention relates generally to valves, and more particularly to a valve used in the medical field.

BACKGROUND OF THE INVENTION

In the medical field, it is often necessary to couple a length of tubing to a patient's blood vessel so as to dispense fluid into the vessel. Rather than pierce the patient's skin a further time, it is advantageous to use the same tubing for other medical purposes as well. For example, during angiographic procedures and other interventional imaging operations, contrast media is typically injected under high pressure through the tubing to a catheter inserted into an artery to generate a radiographic image of the arterial network or other associated location for diagnostic and treatment purposes. The tubing may also be coupled to a pressure transducer by which to obtain the patient's blood pressure in the artery via the hydrostatic column created within the tubing.

Contrast media injection typically requires extremely high pressures, such as 300 psi, and possibly even exceeding 1000 psi. To achieve such pressures, a manual or power injector syringe is typically used. But blood pressure transducers are very sensitive devices designed for low-pressure environments, such as below 2 psi, thus presenting significant challenges when coupled to the same tubing used for high pressure purposes, such as contrast media injection by way of example. In that regard, if steps are not taken to protect the pressure transducer, it could be damaged.

To prevent such damage, a three-way stopcock with three ports may be used. One port is coupled to the transducer (such as via a further length of tubing which may also couple to a saline source), a second port is coupled to the syringe (either directly or via a still further length of tubing), and the third port is coupled to the tubing going to the patient. The stopcock has a lever that can be rotated back and forth between two positions. In one position, the transducer port is fluidicly coupled to the tubing port and the syringe port is fluidicly uncoupled from both the transducer port and the tubing port. In that position, the pressure transducer can sense pressure in the hydrostatic column of the patient tubing. In the other position, the syringe port is fluidicly coupled to the tubing port and the transducer port is fluidicly uncoupled from both the syringe port and the tubing port. In this other position, the contrast media may be injected. At all times, the transducer and syringe ports are fluidicly uncoupled. As a consequence, the pressure transducer is not exposed to fluid or pressure communication with the high pressure source (i.e., the syringe). Further, during high pressure excursions, such as during a contrast media injection, the pressure transducer is not exposed to the tubing through which the high pressure fluid is being injected.

While a stopcock thus can be used to help prevent damage to the blood pressure transducer, it is not without its drawbacks. A stopcock must be manually manipulated, which can interfere with or slow down the medical diagnostic procedure. Moreover, if the lever is not rotated to the desired position, the injection may not be given when or as desired or a valid blood pressure reading may not be obtained.

Another approach to protecting the transducer from exposure to the high pressure during an injection is an automatic manifold which has a series of valves, actuators and/or pistons that respond to the presence or absence of various pressure or signals to selectively couple the tubing to either the syringe or the transducer. Such manifolds have drawbacks as well, including that they are bulky, have several operating components, and are not well suited to use with manual syringes, for example.

SUMMARY OF THE INVENTION

The present invention provides a simple, non-bulky valve that does not require several operating components or manual manipulation, but which operates automatically in both power operated and manually operated systems to allow high pressure fluid flow when desired while automatically providing protection for the pressure transducer as needed. To that end, and in accordance with the principles of the present invention, a valve is provided with a housing and a valve element therein which normally fluidicly couples the transducer and tubing along a first flow path including a flexible control wall which normally interrupts a second flow path between the syringe and the tubing, but which flexes, in response to high pressure excursions from the syringe to allow the second flow path to open as it flexes into the first flow path to thereby restrict same thus providing protection to the transducer during the high pressure excursion from the syringe. While it need not necessarily do so, the control wall may flex sufficiently to fully occlude the first flow path. The control wall flexes back to shut off the second flow path and fully re-establish the first flow path when the high pressure excursion ends.

The housing may have three ports, one for coupling to the transducer, one for coupling to the syringe, and one for coupling to the patient tubing. The valve element advantageously includes the control wall that defines the two fluid paths between the transducer port and the tubing port and between the syringe port and the tubing port, respectively. The valve element also advantageously has a contact member normally bearing against a valve seat associated with the second flow path so as to close off that flow path while the first flow path is normally open. The contact member is responsive to high pressure at the syringe port which causes the contact member to move away from the valve seat to thus open the second flow path for the fluid from the syringe to flow from the syringe port to and out of the tubing port. As that occurs, the control wall flexes into the first flow path, tending to restrict or completely shut off that flow path. When the high pressure excursion ends, the contact member moves back against the valve seat to thus close off the second flow path, and the control wall flexes back out of the first flow path to fully reopen same and reestablish conditions necessary for proper operation of the transducer.

The valve of the present invention may also be used in a reverse fashion. In that regard, if the tubing port is, effectively, sealed, creating a negative pressure at the transducer port will be deemed the same as directing high pressure at the control wall through the syringe port, such that control wall will flex allowing the second flow path to open. This arrangement can be useful where the valve is to be used to control selective filling of an injector syringe, for example.

The contact member may be part of the control wall, and the valve seat may be part of the valve housing. Advantageously, the control wall is generally planar and generally flat, so as to define opposed surfaces, one of which forms part of the second flow path and the other of which forms part of the low pressure path. The first flow path may include a portion that is D-shaped in cross-section, with the control wall defining the flat part of that shape. The valve element may also include a conical section, with a trough therein to define a portion of the second flow path, one wall of the trough, such as the bottom wall, advantageously defining the control wall.

The valve element may be a solid, elastomeric body with a passage extending therethrough to define the first flow path, and a trough having a flexible wall to define at least part of the second flow path. The flexible wall advantageously defines the control wall that also forms part of the first flow path and is adapted to flex into that first flow path in response to high pressure directed at the control wall so as to temporarily restrict the first flow path.

By virtue of the foregoing, there is thus provided a simple, non-bulky valve that does not require several operating components or manual manipulation, but which operates automatically in both power operated and manually operated systems to allow high pressure fluid flow when desired while automatically providing protection for the pressure transducer as needed. These and other objects and advantages of the present invention shall become more apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

Figure 1:
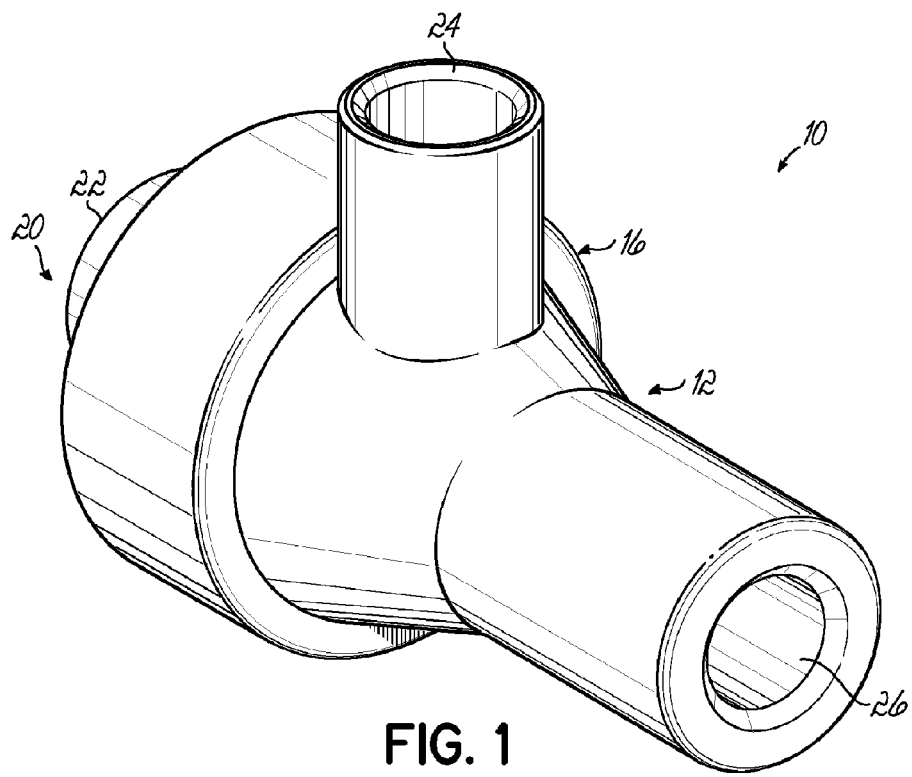
FIG. 1 is an enlarged perspective view of one embodiment of a valve in accordance with the principles of the present invention.
Figure 2:
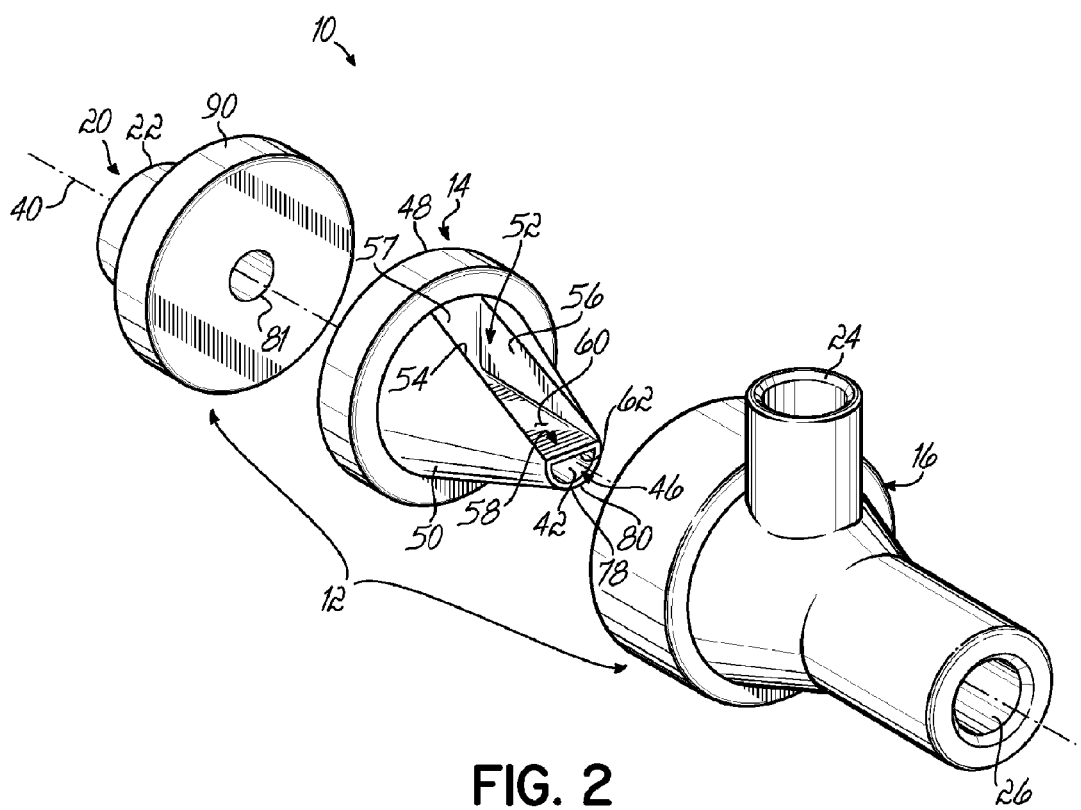
FIG. 2 is an exploded perspective view of the valve of FIG. 1.
Figure 3:
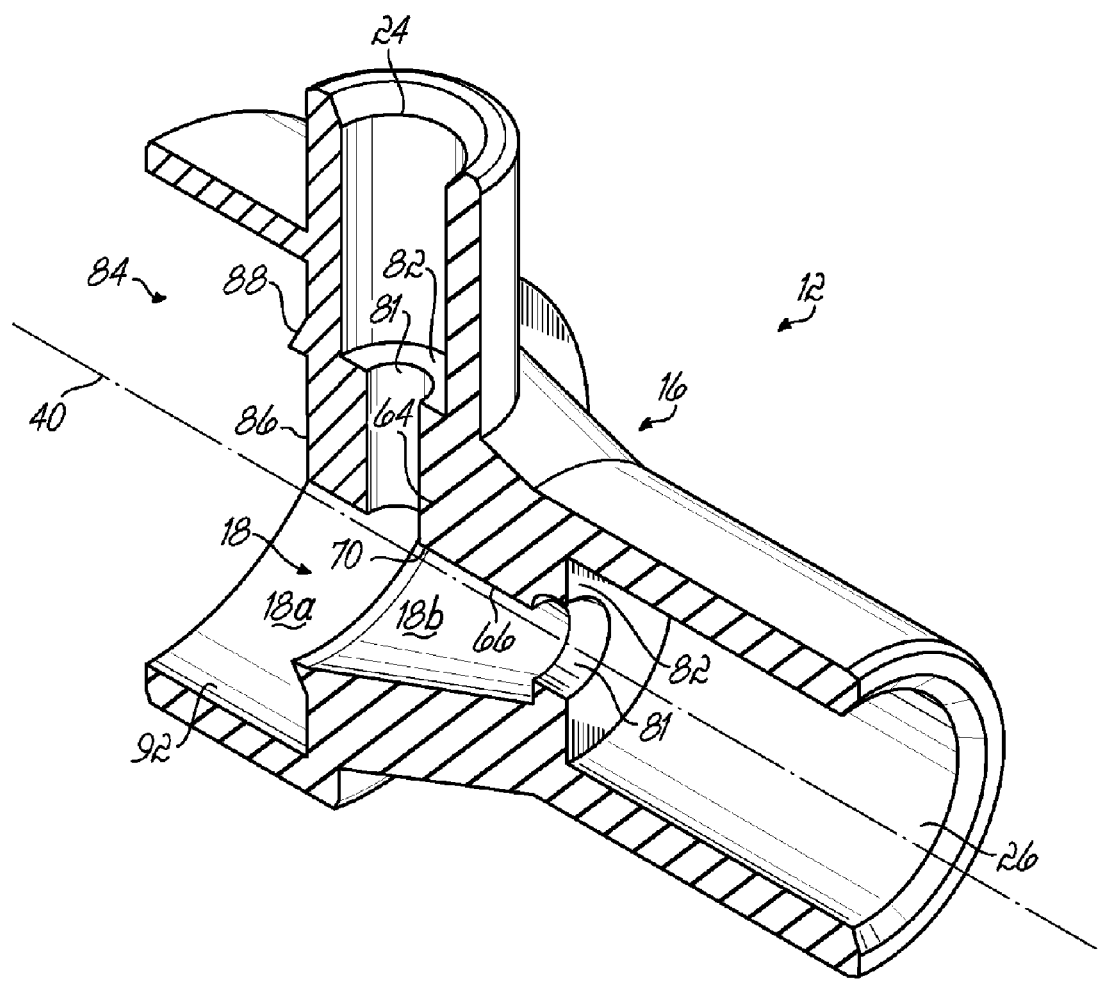
FIG. 3 is a cross-sectional perspective view of the main body portion of the housing of the valve of FIG. 1.

With reference to FIGS. 1 through 5, there is shown one embodiment of a valve 10 according to the principles of the present invention. Valve 10 has a housing 12 and a valve element 14 situated within housing 12. Housing 12 includes a rigid plastic main body portion 16 defining a chamber 18 sized to receive valve element 14 therein, and a rigid plastic end cap 20 to securably retain valve element 14 within chamber 18.

Figure 6:
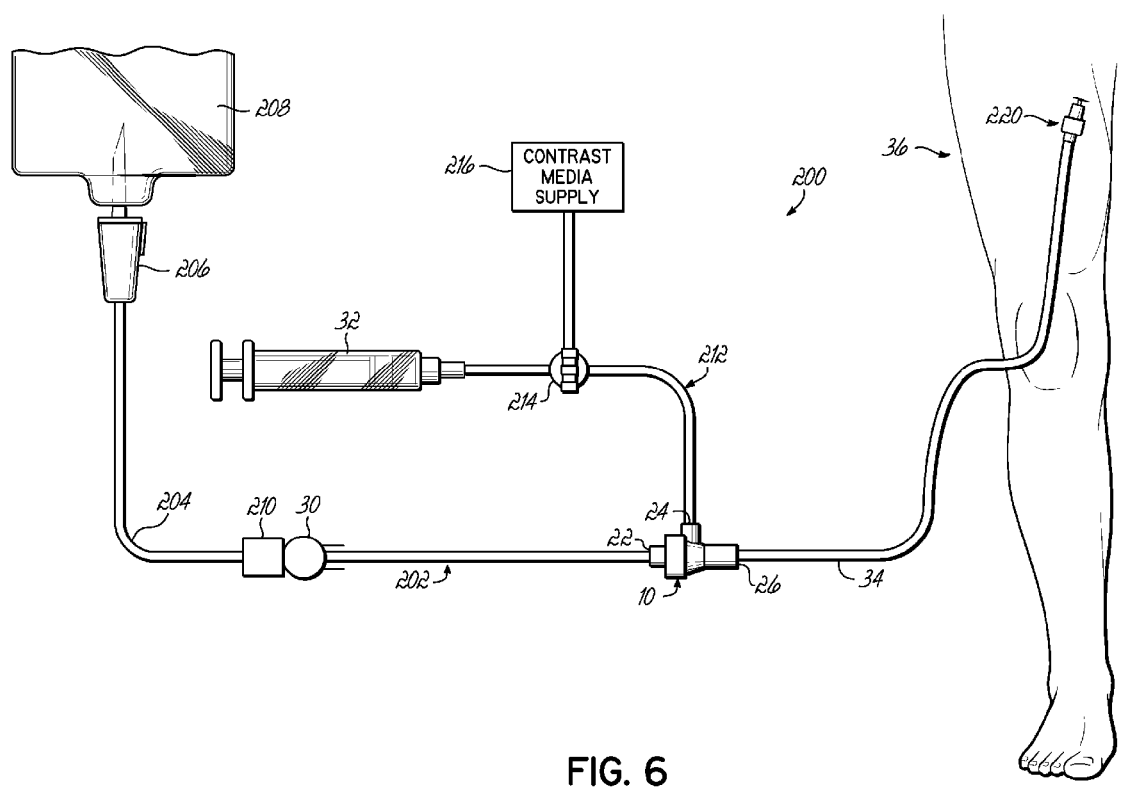
FIG. 6 is a schematic view of one embodiment of a contrast dispensing system incorporating the valve of FIG. 1.

Housing 12 includes three ports, 22, 24, 26, with port 22 being designated as a low pressure port and which may be coupled to a low pressure operating device such as a pressure transducer 30 (FIG. 6), port 24 being designated as a high pressure port and which may be coupled to a high pressure generating source such as an injector syringe 32 (FIG. 6), and port 26 being designated as a common or tubing (or patient tubing) port and which may be coupled to patient tubing 34 (FIG. 6) to communicate with the circulatory system of a patient 36 (FIG. 6). In the embodiment shown, chamber 18 has a disc-shaped section 18a and a conical shaped section 18b both along an axis 40 with ports 22 and 26 being coaxial therewith.

Valve element 14 is a solid, elastomeric body having a passage 42 extending therethrough between front and back openings 44, 46. Back opening 44 is formed in disc-shaped portion 48 of valve element 14 which is sized to fit snugly within disc-shaped section 18a of housing 12. Valve element 14 also includes a conical portion 50 having a trough 52 formed therein to fit snugly within conical section 18b of housing 12. With valve element 14 so-received, openings 44 and 46 are aligned with ports 22 and 26 along axis 40 such that passageway 42 defines a first flow path between ports 22 and 26. Trough 52 has left and right side walls 54, 56, back wall 57, and bottom wall 58. Bottom wall 58 is resilient so that it may flex to define a control wall, but when not flexed, is generally planar and generally flat so as to define opposed upper and lower surfaces 60 and 62, for purposes to be hereinafter described.

Figure 4:
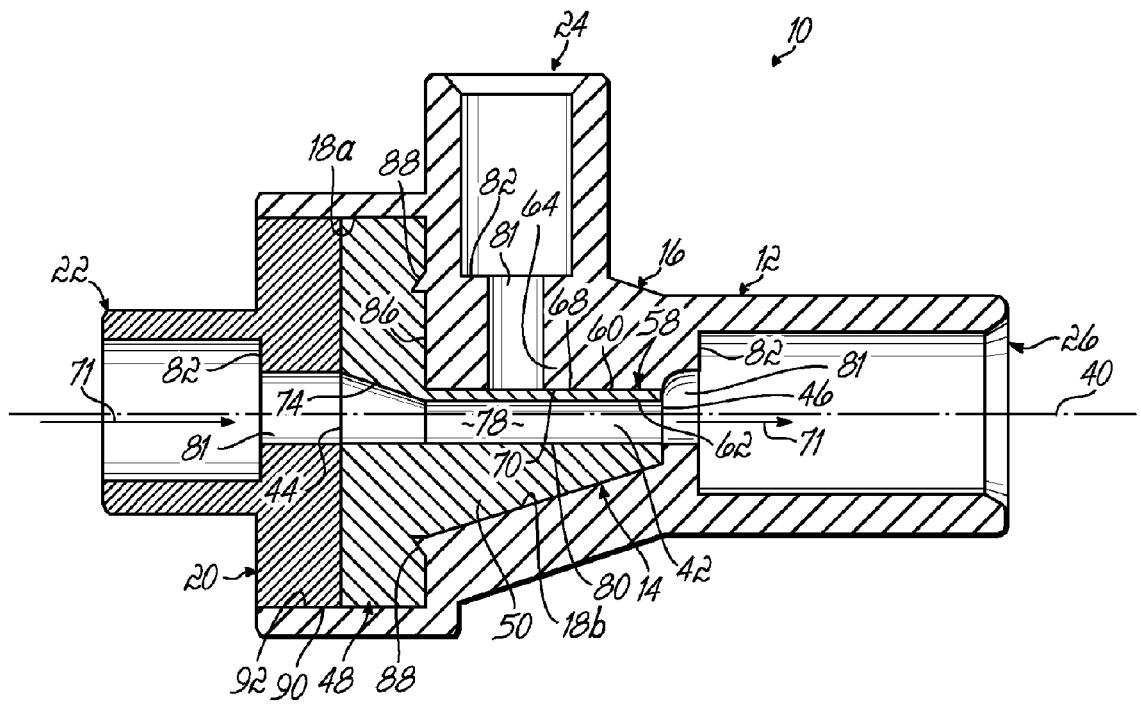
FIGS. 4 and 5 are cross-sectional views of the valve of FIG. 1 in different stages of operation for the purposes of explaining the principles of the present invention.
Figure 5:
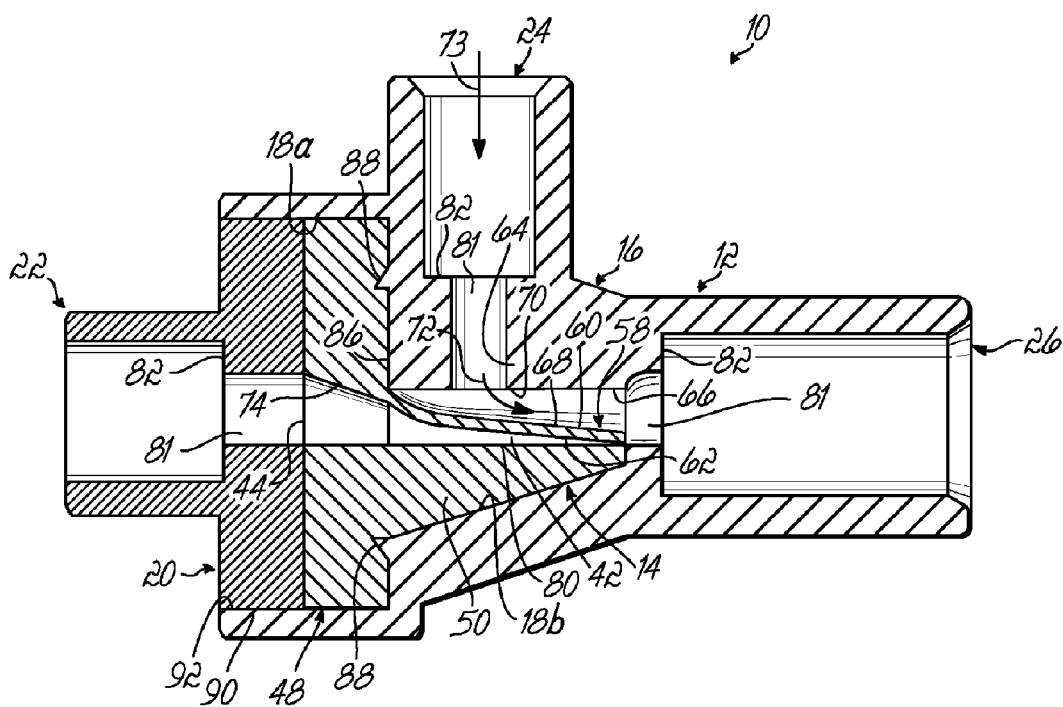

Housing 12 includes a projecting portion 64 that is sized and shaped to extend into chamber 18 below high pressure port 24 and sized to fit snugly within trough 52. Projecting portion 64 includes a generally flat surface 66 to confront upper surface 60 of control wall 58. A contact member 68 supported on control wall 58, and which is advantageously defined by a portion of control wall 58 upper surface 60, normally bears against surface 66, which defines a valve seat thereat (as at 70, it being understood that contact member 68 and valve seat 70 are advantageously defined by and along surfaces 60 and 66) to occlude flow between ports 24 and 26 with flow path 42 open as indicated by arrows 71 (FIG. 4). However, high pressure at port 24 (as indicated by arrow 73 in FIG. 5) directed at surface 60 of control wall 58 causes control wall 58 to flex away from the pressure thereby causing contact member 68 to come away from valve seat 70 to thus open a second flow path 72 (FIG. 5) between ports 24 and 26, including along upper surface 60. When the high pressure excursion ends, the resiliency of control wall 58 causes it to return toward its unflexed state such that contact member 68 bears against surface 66 and/or valve seat 70 thereof, to occlude second flow path 72 and restore first flow path 42.

Control wall 58, and especially the underside surface 62 thereof, defines a flat portion of passageway 42 such that passage 42 necks down at 74 from cylindrical opening 44 to a D-shaped portion 78 in conical portion 50 in the area of control wall 58. First flow path 42 thus extends along surface 62 of control wall 58 to opening 46 which may also be D-shaped. Passageway portion 78 also includes an arcuate flow wall portion 80 opposite control wall 58 (and which is an extension of the cylinder wall in area 74). As control wall 58 flexes to open the second flow path 72, a portion of control wall 58 flexes into passageway 42 in portion 78 and toward arcuate flow wall portion 80 (which generally remains in position due to interaction of conical valve element portion 50 and conical section 18b of housing body portion 18) to thus restrict the first flow path 42. The D-shape of passageway portion 78 aids in proper operation of control wall 58. In that regard, rather than having to buckle, as would be the case for an arcuate wall portion like flow wall portion 80, control wall 58 merely needs to expand or flex, as more readily occurs because the surface area of upper surface 60 of control wall 58 is smaller than the area of arcuate wall portion 80. Control wall 58 may flex sufficiently to come into contact with wall portion 80 sufficiently to occlude passageway 42 in portion 78. Even when not occluded, the restriction reduces the exposure to a transducer 30 coupled to port 22 during high pressure excursions.

Control wall 58 thus operates automatically, and in response to high pressure excursions at port 24, to control opening of second flow path 72 and restricting of first flow path 42. Note that a negative pressure at port 22, with port 26 effectively sealed, will have the effect of a high pressure directed at surface 60 of control wall 58 thus causing second flow path 72 to open.

Each port 22, 24, and 26 may communicate through a bore 81 into or against the associated aspect of the valve element 14 to thus define a flange 82 directed at the port. The flange 82 cooperates with the associated port to limit insertion of a length of tubing as will be readily appreciated. Main body portion 18 of housing 12 has an open back end as at 84 (FIG. 3) which receives therein end cap 20. A flange wall 86 extends between disc-shaped section 18a and conical section 18b and defines a seat for disc-shaped valve element portion 48 to bear against when end cap 20 secures valve element 14 within housing 12. Flange wall 86 may include one or more barbs 88, which may be in the form of an annular projecting ring, to assist in securing valve element 14 within housing 12. End cap 20 may also include such barbs (not shown) if desired. End cap 20 is secured to housing 12 such as by frictional engagement between the periphery 90 thereof (which may be roughened or have projections or barbs if desired but not shown) and the inner surface 92 of open back end 84 and/or by ultrasonic welding, by way of example.

As used herein, the terms "high pressure" and "low pressure" are merely relative terms intended to describe the different pressures experienced by the first and second flow paths 42 and 72, and as a convenient reference for the ports of valve 10. As to the latter, the terms are being used merely to designate which port is being discussed, and not to limit their use in regard to the actual pressures to be encountered thereat. As to the former, in its broadest context, high pressure is encountered when the pressure directed at control wall surface 60 (either by high pressure via port 24 or negative pressure at port 22 with port 26 effectively sealed) is greater than the pressure in first flow path 42, and particularly closer to port 26, such that contact member 68 will generally respond by moving away from valve seat 70. In some instances, however, valve 10 may advantageously be designed to allow flow in the second flow path only when the pressure at port 24 exceeds a predetermined cracking pressure. In such instances control wall 58 is intended to remain in place with contact member 68 bearing against valve seat 70 until the pressure at port 24 exceeds the cracking pressure. The cracking pressure is selected for the particular purpose of the valve 10. Where a blood pressure transducer 30 is to be used, the cracking pressure may be selected to be at least approximately 2 psi in order to reduce the risk of exposure of transducer 30 to pressures thereabove. The cracking pressure is determined generally by the size, thickness and durometer of control wall 58 as will be readily appreciated by those skilled in the art.

With reference to FIG. 6, valve 10 may be employed in a contrast media injection system 200. Low pressure port 22 of valve 10 is coupled to a length of tubing 202 coupled to pressure transducer 30 (which may include a sensor and/or a disposable dome), which in turn is coupled via a further length of tubing 204 to a spike 206 coupled to a saline bag 208 (which may be pressurized). A flush valve 210 may be included as well upstream of transducer 30. High pressure port 24 of valve 10 is coupled via tubing 212 to injector syringe 32 (which shown here is a manual syringe but could also be a power injector syringe). A valve 214, such as a stopcock, may be located in tubing 212 between syringe 32 and valve 10 for selectively coupling syringe 32 to a contrast media supply 216 as will be recognized in the art. Supply 216 may be a bag or bottle of contrast media or may include a reservoir and related components as shown in U.S. Pat. No. 6,800,072. Common port 26 of valve 10 is coupled to a length of patient tubing 34 communicating with the circulatory system, such as an artery, of a patient 36 via a catheter 220 or the like as is conventional.

In use, a hydrostatic column is normally established in tubing 34 and valve 10 is in its nominal or first state such that first flow path 42 is open and communicating the hydrostatic column to transducer 30 with second flow path 72 generally occluded (FIG. 4). In that first state, transducer 30 is operating normally to provide a signal representative of the patient's arterial blood pressure. When a high pressure excursion is experienced at port 24, such as when syringe 32 is activated to inject contrast media toward tubing 34 and into patient 36, valve 10 goes into a second state shown in FIG. 5. In that second state, the high pressure excursion directed at surface 60 of control wall 58 causes control wall 58 to flex thereby opening up the second flow path 72 for the contrast media to flow out of port 26 and into tubing 34. Syringe 32 typically injects the contrast media at pressures ranging from approximately 300 psi to approximately 1200 psi. Ordinarily, these pressures would cause significant damage to pressure transducer 30. However, at the same time that path 72 is opening, control wall 58 flexes into first flow path 42 to thereby restrict, and possibly occlude, same to thereby limit the exposure of transducer 30 to that high pressure excursion. When the high pressure excursion ends, control wall 58 tends to unflex thereby re-occluding the second flow path 72 and re-establishing the first flow path 42 for normal operation of transducer 30.

Figure 7:
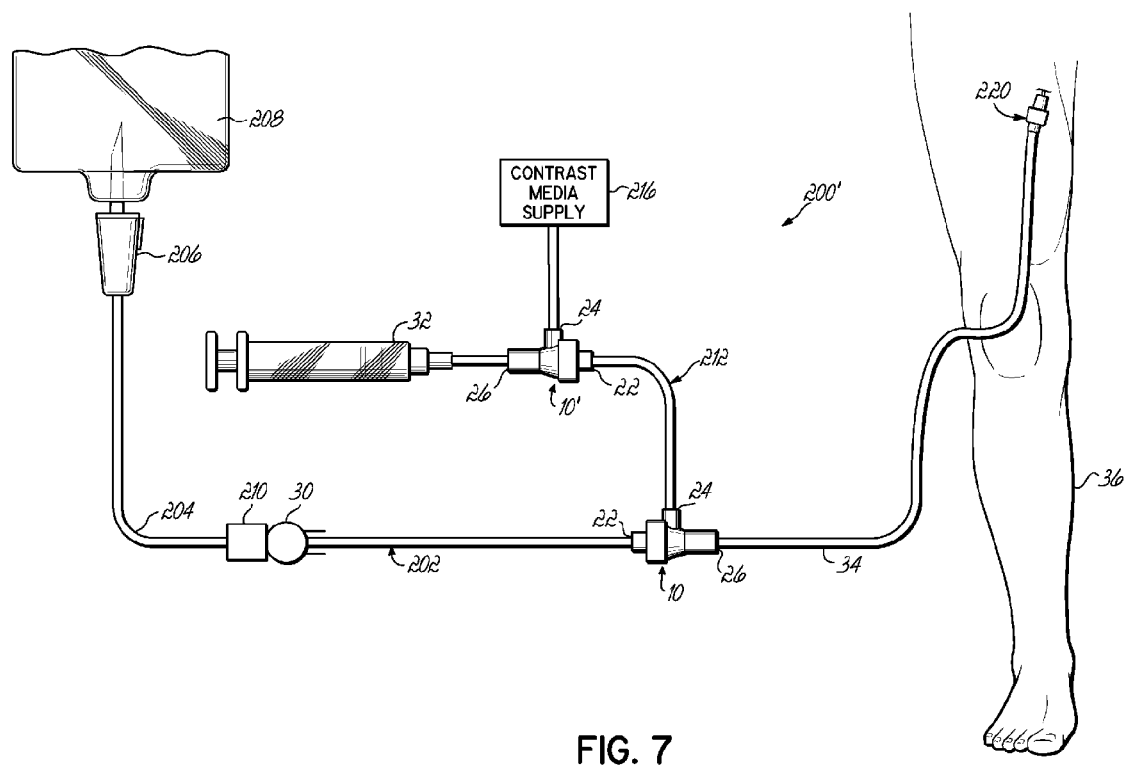
FIG. 7 is a schematic view of an embodiment of a contrast dispensing system similar to that of FIG. 6 incorporating two of the valves of FIG. 1.

In the embodiment of FIG. 6, the valve 214 is a stopcock. As an alternative, and with reference to FIG. 7, a modified system 200' may be provided which is generally like system 200 but in which valve 214 is replaced with a second valve 10' like valve 10, but in a reverse fashion. Thus, low pressure port 22 of valve 10' is coupled to high pressure port 24 of valve 10, high pressure port 24 of valve 10' is coupled to the contrast media supply 216, and common port 26 of valve 10' is coupled to the syringe 32. In that case, when contrast media is to be pulled into the syringe 32, a negative pressure is caused to bear against the lower surface 62 of the control wall 58 in valve 10' which, for purposes herein, is deemed to be a high pressure excursion at surface 60 thereof such that valve 10' goes into the second state to allow media from supply 216 to fill syringe 32 via the second flow path 72 thereof. When syringe 32 is no longer pulling the media into it, or when it is activated to expel or dispense the media to the patient 36, that negative pressure ceases (which in this context means the high pressure excursion at surface 60 thereof has ended) such that the flow path 72 thereof closes and flow path 42 is no longer restricted thereby allowing the media to operate on valve 10 as above-described.

By virtue of the foregoing, there is thus provided a simple, non-bulky valve that does not require several operating components or manual manipulation, but which operates automatically in both power operated and manually operated systems to allow high pressure fluid flow when desired while automatically providing protection for the pressure transducer as needed.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art.

For example, housing 12 could be in the form of a Y-site rather than the T-site generally shown herein. Additionally, valve seat 70 may be defined by a different surface of housing 12 or even by a portion of valve element 14. And further, contact member 68 may be supported be some portion of valve element 14 other than control wall 58. Also, while valve 10 has been shown in a contrast media injection system and with the low pressure port coupled to a transducer, it could be used in other systems where a first fluid is to be normally coupled such as along first flow path 42 of valve 10, and wherein a second fluid is to be selectively coupled, such as by introduction through port 24. Thus, it will be seen that valve 10 also operates as a back check valve against flow in first flow path 42 accessing port 24 via the second flow path. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A valve, comprising:
a housing having a low pressure fluid port, a high pressure fluid port, and a common port; and
a valve element situated within the housing between the ports, the valve element having a body and a generally flat control wall with first and second surfaces, the control wall included in the body, a first flow path extending through the body and along the first surface of the control wall and coupling the low pressure fluid port to the common port, and a second flow path extending along the second surface of the control wall and coupling the high pressure fluid port to the common port, the valve element further having a contact member normally bearing against a valve seat associated with the second flow path so as to occlude the second flow path, the contact member being responsive to high pressure at the high pressure fluid port so as to move away from the valve seat and thereby open the second flow path, the control wall flexing into the first flow path in response to such opening.

2. The valve of claim 1, the valve seat being a portion of the housing.

3. The valve of claim 1, the first and second surfaces being positioned on opposite sides of the control wall.

4. The valve of claim 1, the control wall supporting the contact member.

5. The valve of claim 4, a portion of the second surface defining the contact member.

6. The valve of claim 1, the control wall being adapted to restrict the first flow path when flexing in response to the opening of the second flow path.

7. The valve of claim 6, the first flow path having a flow wall opposite the control wall, the control wall being adapted to contact the flow wall when flexing into the first flow path so as to occlude said flow path.

8. The valve of claim 1, the contact member being responsive to a pressure at or above a predetermined cracking pressure, the cracking pressure being at least approximately 2 psi.

9. The valve of claim 1, the first flow path having a portion with a D-shaped cross-section, the control wall defining part of the D-shaped portion.

10. A valve comprising:
a housing having a low pressure fluid port, a high pressure fluid port, and a common port; and
a valve element situated within the housing between the ports, the valve element having a control wall with first and second surfaces, a first flow path extending along the first surface of the control wall and coupling the low pressure fluid port to the common port, and a second flow path extending along the second surface of the control wall and coupling the high pressure fluid port to the common port, the valve element further having a contact member normally bearing against a valve seat associated with the second flow path so as to occlude the second flow path, the contact member being responsive to high pressure at the high pressure fluid port so as to move away from the valve seat and thereby open the second flow path, the control wall flexing into the first flow path in response to such opening, the valve element having a conical portion through which the first flow path extends and a trough in the conical portion defining a portion of the second flow path.

11. The valve of claim 10, the trough having a left side, a right side, and a bottom side interconnecting the left and right sides, one of the sides of the trough defining the control wall.

12. The valve of claim 11, the bottom side defining the control wall.

13. The valve of claim 1, further comprising:
an end cap received in the low pressure fluid port of the housing, the end cap having an inlet passage in fluid communication with the first flow path of the valve element.

14. A valve comprising:
a housing having a low pressure fluid port, a high pressure fluid port, and a common port;
a valve element situated within the housing between the ports, the valve element having a control wall with first and second surfaces, a first flow path extending along the first surface of the control wall and coupling the low pressure fluid port to the common port, and a second flow path extending along the second surface of the control wall and coupling the high pressure fluid port to the common port, the valve element further having a contact member normally bearing against a valve seat associated with the second flow path so as to occlude the second flow path, the contact member being responsive to high pressure at the high pressure fluid port so as to move away from the valve seat and thereby open the second flow path, the control wall flexing into the first flow path in response to such opening; and
an end cap received in the low pressure fluid port of the housing, the end cap having an inlet passage in fluid communication with the first flow path of the valve element, the end cap frictionally engaging the housing to retain the valve element within the housing.

15. The valve of claim 14, the end cap having an outer portion with one or more barbs to facilitate frictionally engaging the housing.

16. The valve of claim 13 wherein the end cap is ultrasonically welded to the housing to retain the valve element within the housing.

17. The valve of claim 13, the housing having a flange with at least one barb adapted to engage an outer surface of the valve element.

18. The valve of claim 17, the at least one barb having an annular configuration on the flange of the housing.

19. The valve of claim 13, the first flow path having a portion with a D-shaped cross-section and a transition portion positioned between the D-shaped portion and the inlet passage of the end cap, the control wall defining part of the D-shaped portion.

20. A valve, comprising:
a housing having a low pressure fluid port, a high pressure fluid port, and a common port; and
a valve element situated within the housing between the ports, the valve element having a body and a generally flat control wall with first and second surfaces, the control wall included in the body, a first flow path extending through the body and along the first surface of the control wall and coupling the low pressure fluid port to the common port, and a second flow path extending along the second surface of the control wall and coupling the high pressure fluid port to the common port, a portion of the second surface normally bearing against an inner surface of the housing so as to occlude the second flow path, the control wall being responsive to high pressure at the high pressure fluid port so as to move away from the inner surface of the housing and thereby open the second flow path, the control wall flexing into and occluding the first flow path in response to such opening.

21. A valve element, comprising:
a solid body having first and second ports, a passage extending from the first port to the second port to define a first flow path, and an outer portion with a trough formed therein, the trough having a flexible side defining a generally flat control wall between the trough and the first flow path, the control wall adapted to flex into the first flow path in response to high pressure directed at the control wall so as to temporarily restrict the first flow path.

22. A valve element comprising:
a solid body having first and second ports, a passage extending from the first port to the second port to define a first flow path, and an outer portion with a trough formed therein, the trough having a flexible side defining a generally planar control wall between the trough and the first flow path, the control wall adapted to flex into the first flow path in response to high pressure directed at the control wall so as to temporarily restrict the first flow path, the control wall being generally planar.

23. The valve element of claim 22, the outer portion being conical.

24. A valve element comprising:
a solid body having first and second ports, a passage extending from the first port to the second port to define a first flow path, and an outer portion with a trough formed therein, the trough having a flexible side defining a control wall between the trough and the first flow path, the control wall adapted to flex into the first flow path in response to high pressure directed at the control wall so as to temporarily restrict the first flow path, the first flow path having a portion with a D-shaped cross-section, the control wall defining part of the D-shaped portion.

25. The valve element of claim 24, the first port being substantially circular, the first flow path further including a transition portion with positioned between the first port and the D-shaped portion.

26. The valve element of claim 21, the outer portion being conical.

27. The valve element of claim 21, the control wall being responsive to sufficiently high pressure directed at said wall so as to flex into the first flow path sufficient to occlude said flow path.

28. The valve element of claim 21, the control wall being responsive to a pressure at or above a predetermined cracking pressure, the cracking pressure being at least approximately 2 psi.

29. A method of controlling the flow of low pressure fluid and high pressure fluid to a supply line, comprising:
placing the supply line in fluid communication with a common port of a housing, the housing having a low pressure port for receiving the low pressure fluid and a high pressure port for receiving the high pressure fluid;
communicating the low pressure fluid through a first flow path being defined through a body of a valve element situated within the housing between the ports, the first flow path coupling the low pressure fluid port to the common port, the body of the valve element having a generally flat control wall with a first surface defining a portion of the first flow path and a second surface defining a portion of a second flow path, the second flow path coupling the high pressure port to the common port, the valve element further including a contact member normally bearing against a valve seat associated with the second flow path, the contact member being responsive to high pressure at the high pressure fluid port; and
communicating high pressure fluid to the high pressure fluid port so as to move the contact member away from the valve seat and thereby open the second flow path, the control wall flexing into the first flow path in response to such opening.

30. The method of claim 29, the control wall restricting the first flow path when flexing in response to the high pressure fluid communicated to the high pressure fluid port.

31. The method of claim 30, the control wall occluding the first flow path when flexing in response to the high pressure fluid communicated to the high pressure fluid port.

32. The method of claim 29, the high pressure fluid being communicated at a pressure at or above a predetermined cracking pressure of the control wall, the cracking pressure being at least approximately 2 psi.

33. The method of claim 29, the first flow path having a portion with a D-shaped cross-section, the control wall defining part of the D-shaped portion.

34. The method of claim 29, further comprising:
receiving an end cap in the low pressure fluid port to retain the valve element within the housing, the end cap having an inlet passage in fluid communication with the first flow path of the valve element.

35. A method of controlling the flow of low pressure fluid and high pressure fluid to a supply line, comprising:
placing the supply line in fluid communication with a common port of a housing, the housing having a low pressure port for receiving the low pressure fluid and a high pressure port for receiving the high pressure fluid;
communicating the low pressure fluid through a first flow path being defined through a body of a valve element situated within the housing between the ports, the first flow path fluidicly coupling the low pressure fluid port to the common port, the body of the valve element further including a generally flat control wall with a first surface defining a portion of the first flow path and a second surface normally bearing against an inner surface of the housing, the control wall being responsive to high pressure at the high pressure fluid port; and communicating high pressure fluid to the high pressure fluid port so as to flex the control wall away from the inner surface of the housing and into the first flow path to thereby form a second flow path between the second surface and the inner surface, the second flow path fluidicly coupling the high pressure fluid port to the common port.

36. The valve element of claim 22, the control wall being responsive to sufficiently high pressure directed at said wall so as to flex into the first flow path sufficient to occlude said flow path.

37. The valve element of claim 22, the control wall being responsive to a pressure at or above a predetermined cracking pressure, the cracking pressure being at least approximately 2 psi.

38. The valve element of claim 24, the control wall being responsive to sufficiently high pressure directed at said wall so as to flex into the first flow path sufficient to occlude said flow path.

39. The valve element of claim 24, the control wall being responsive to a pressure at or above a predetermined cracking pressure, the cracking pressure being at least approximately 2 psi.

* * * * *

UNITED STATES PATENT AND TRADEMARK OFFICE
CERTIFICATE OF CORRECTION

| | | |
|---|---|---|
| PATENT NO. | : 7,302,960 B2 | Page 1 of 1 |
| APPLICATION NO. | : 11/163660 | |
| DATED | : December 4, 2007 | |
| INVENTOR(S) | : Charles R. Patzer | |

It is certified that error appears in the above-identified patent and that said Letters Patent is hereby corrected as shown below:

<u>Claim 25</u>

Line 64 – "transition portion with positioned between" should be -- transition portion positioned between --

Signed and Sealed this

Twelfth Day of August, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,302,960 B2 | Page 1 of 1 |
| APPLICATION NO. | : 11/163660 | |
| DATED | : December 4, 2007 | |
| INVENTOR(S) | : Charles R. Patzer | |

It is certified that error appears in the above-identified patent and that said Letters Patent is hereby corrected as shown below:

Column 9, Claim 25

Line 64 – "transition portion with positioned between" should be -- transition portion positioned between --

This certificate supersedes the Certificate of Correction issued August 12, 2008.

Signed and Sealed this

Sixteenth Day of September, 2008

JON W. DUDAS
*Director of the United States Patent and Trademark Office*